(12) United States Patent
Williams et al.

(10) Patent No.: US 6,408,214 B1
(45) Date of Patent: Jun. 18, 2002

(54) DEFLECTABLE TIP CATHETER FOR CS PACING

(75) Inventors: Terrell M. Williams, Brooklyn Park; Kenneth C. Gardeski, Plymouth, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/614,131

(22) Filed: Jul. 11, 2000

(51) Int. Cl.⁷ ................................................. A61N 1/18
(52) U.S. Cl. ...................................................... 607/122
(58) Field of Search ................................ 607/122, 123; 600/373, 374, 372, 381, 382

(56) References Cited

U.S. PATENT DOCUMENTS

| | | |
|---|---|---|
| 4,166,469 A | 9/1979 | Littleford |
| 4,195,637 A | 4/1980 | Gruntzig et al. |
| 4,721,118 A | 1/1988 | Harris |
| 4,863,442 A | 9/1989 | DeMello et al. |
| 5,409,469 A | 4/1995 | Schaerf |
| 5,545,149 A | 8/1996 | Brin et al. |
| 5,755,704 A | 5/1998 | Lunn |
| 5,811,043 A | 9/1998 | Horrigan et al. |
| 5,868,700 A | 2/1999 | Voda |
| 5,921,952 A | 7/1999 | Desmond, III et al. |
| 5,987,746 A | 11/1999 | Williams |
| 5,997,562 A | 12/1999 | Zadno-Azizi et al. |
| 6,038,472 A | 3/2000 | Williams et al. |
| 6,061,588 A | 5/2000 | Thornton et al. |

FOREIGN PATENT DOCUMENTS

| | | |
|---|---|---|
| WO | WO 99/15078 | 4/1999 |
| WO | WO 00/04948 | 2/2000 |

*Primary Examiner*—Scott M. Getzow
(74) *Attorney, Agent, or Firm*—Girma Wolde Michael; Michael C. Soldner

(57) ABSTRACT

A deflectable tip introducer or guide catheter optimized for placement of leads or catheters within the vasculature of the human body is disclosed. The introducer includes inner and outer concentrically located tubular sheaths. The inner and outer sheaths are preferably provided with different curved configurations, allowing the over-all displayed curvature of the introducer over its distal portion to be adjusted by longitudinal movement of the inner and outer sheaths relative to one another. The outer sheath may be fabricated of a thin tube of polyetheretherketone (PEEK) or other material having a relatively large stiffness as compared to the inner sheath. The outer sheath is sized to fit closely around the inner sheath. The inner sheath may be formed of a reinforced polyurethane, and preferably has a thin wall that is of about 0.005 inches in thickness or less. When supported by the inner sheath, the outer sheath transfers torque along the composite introducer assembly and serves to modify the curved configuration displayed by the distal end of the introducer assembly in conjunction with the relative longitudinal movement of the inner and outer sheaths.

32 Claims, 4 Drawing Sheets

DEFLECTABLE TIP CATHETER FOR CS PACING

BACKGROUND OF THE INVENTION

The present invention is directed toward medical catheters and leads generally, and more particularly is directed toward mechanisms for introduction of leads and catheters into the human body.

Introducers and guide catheters are widely employed to place indwelling electrode leads and catheters in desired locations within the body. These devices typically take the form of elongated tubular sheaths, which may be straight or curved in configuration, through which the lead or catheter to be placed is advanced. Examples of introducers employed to facilitate entry of leads into the vasculature are disclosed in U.S. Pat. No. 4,166,469 issued to Littleford and U.S. Pat. No. 5,409,469 issued to Schaerf et al. Introducers or guide catheters of substantially greater length, provided with preformed curvatures or deflection mechanisms to facilitate locating the tip of a lead or catheter after it has been substantially advanced into the vascular system of a patient are also well known. Examples of such guide catheters are disclosed in U.S. Pat. No. 4,195,637 issued to Gruntzig et al. and U.S. Pat. No. 5,868,700 issued to Voda et al. An alternative mechanism for directing an indwelling electrode lead or catheter is to provide a two-piece structure including inner and outer tubes which may be moved relative to one another to provide distal sections with controllable adjustable curvatures.

SUMMARY OF THE INVENTION

The present invention is directed toward an improved deflectable tip introducer or guide catheter (hereafter referred to as an introducer) optimized for placement of leads or catheters within the vasculature of the human body. In particular, the introducer is optimized for placement of leads in the coronary sinus.

The improved introducer is a two-piece structure including inner and outer concentrically located tubular sheaths, in which the materials of the sheaths are particularly optimized to provide high torque and pushability while providing a minimal cross-sectional area of the wall. The inner and outer sheaths are preferably provided with different curved configurations, so that the over-all displayed curvature of the introducer over its distal portion may be adjusted by longitudinal movement of the inner and outer sheaths relative to one another.

In a preferred embodiment, the inner sheath may have a structure corresponding to the body of a conventional guide catheter, for example, corresponding to the SHERPA® guide catheters sold by Medtronic, Inc. Exemplary structures of similar catheters are disclosed in U.S. Pat. No. 5,755,704 issued to Lunn, U.S. Pat. No. 5,545,149, issued to Brin, et al. and U.S. Pat. No. 5,811,043 issued to Horrigan, et al., all incorporated herein by reference in its entirety. The inner sheath of the introducer may also have a structure corresponding to guide catheters of other types, marketed by Bard, Guidant, Boston Scientific, Cordis, or the like, for example, as disclosed in U.S. Pat. No. 4,863,442 issued to DeMello, et al, U.S. Pat. No. 5,921,952 issued to Desmond III et al., or U.S. Pat. No. 6,061,588 issued to Thorton et al. Typical materials employed for such guide catheters include polyurethanes, polyethylenes, polyesters, polyether block amides, polyamides, polytetrafluoroethylenes and the like, reinforced by polymeric or metallic braids or wires. Alternatively, the inner sheath may take the form of an un-reinforced tube of any of the materials referred to above.

The outer sheath is preferably fabricated of a thin tube of polyetheretherketone (PEEK) polymer (VICTREX® 381G or VICTREX® 450 manufactured by Victrex PLC.) or other material having a relatively large stiffness as compared to the inner sheath. The outer sheath is sized to fit closely (e.g., about 0.007 inches or less total clearance) around the inner sheath, and has a thin wall (e.g. about 0.005 inches in thickness or less). If it is desirable to utilize a slitting tool to remove the outer sheath before the inner sheath after the delivery of the therapeutic or diagnostic device, the clearance between the inner and outer sheaths should not be reduced substantially below 0.020 inches. A PEEK tube of this type, while providing for good torque transfer along its length, would normally not be suitable as an introducer sheath due to a tendency to kink when twisted or bent. However, when supported by the inner sheath, the outer sheath of PEEK tubing, in spite of its thin walls, serves admirably to assist in transfer of torque along the composite introducer assembly and in conjunction with modification of the curved configuration displayed by the distal end of the introducer assembly as a result of relative longitudinal movement of the inner and outer sheaths.

DETAILED DESCRIPTION OF THE PREFERRED EMBODIMENTS

Figure 1:
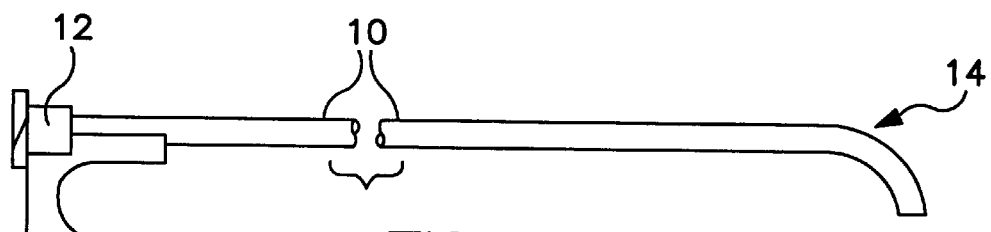
FIG. 1 is a plan drawing of an inner introducer sheath according to the present invention.

FIG. 1 is a plan view of an inner introducer sheath according to the present invention. The introducer sheath comprises an elongated tubular sheath body 10, which, as discussed above, may correspond in structure to conventional guide catheters. Tubular body 10 may also simply be an extruded tube of a biocompatible plastic, as discussed above. As illustrated, the inner sheath may have a slittable luer hub 12 mounted at its proximal end which may correspond to the slittable luer hub disclosed in U.S. patent application Ser. No. 09/116,628 by Gardeski et al, incorporated herein by reference in its entirety. Luer hub 12 is adapted to be split by means of an associated slitting tool to facilitate removal of the inner introducer sheath over a catheter or electrode lead passing therethrough.

As illustrated, the distal end of the inner sheath displays a curve 14, formed into the tubular introducer body 10. As illustrated, curve 14 extends over approximately 90° and has an approximate radius of curvature of about 0.3 to 1.0 inches. This particular curvature is chosen for use in conjunction with an introducer system according to the present invention optimized for use in placement of leads or catheters in the coronary vasculature. Larger curvatures may be employed, but may make placement of leads including rigid electrodes more difficult. Other curved configurations may of course be substituted.

Figure 2:
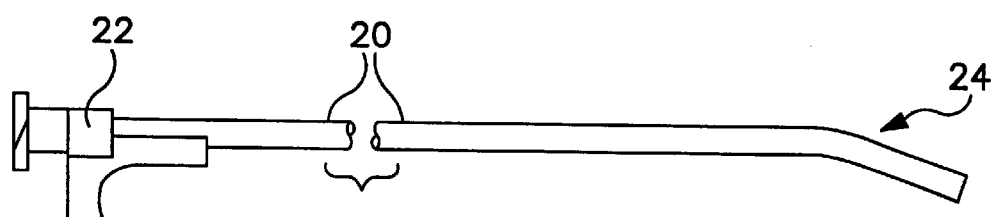
FIG. 2 is a plan drawing of an outer introducer sheath according to the present invention.

FIG. 2 is a plan view of an outer introducer sheath according to the present invention. The outer introducer sheath includes an elongated tubular sheath body 20, which as discussed above, is formed of PEEK polymer having a wall thickness of about 0.005 inches or less. As illustrated, tubular sheath body 20 also may have a slittable luer hub 22 at its proximal end and is provided with a preformed curve 24 at its distal end. Preformed curve 24 extends over an arc of about 70°, and has a radius of curvature of about 0.3 to 2 inches. As discussed above, the configuration of the curve of the outer sheath is also optimized for use in conjunction with an introducer adapted for placement of leads in the coronary vasculature. Other curved configurations could also be substituted.

Figure 3:
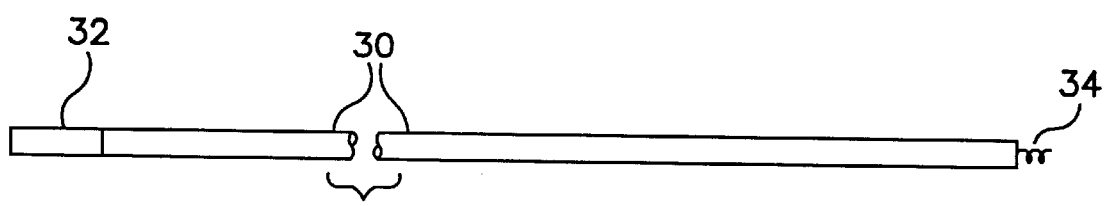
FIG. 3 is a plan drawing of an electrode lead appropriate for introduction through the introducer sheath of the present invention.

FIG. 3 is a plan view of a first embodiment of an electrode lead for use in conjunction with the introducer of the present invention. The lead is provided with an elongated insulative body 30 that carries a conductor therein extending between a connector pin 32 on its proximal end and a helical electrode 34 at its distal end. Electrode 34 is adapted to be screwed into the tissue of the coronary vasculature or into heart tissue at other locations, as may be accessed using the introducer system. In particular, the lead may have a body diameter of approximately one or two French and may employ a stranded or coiled conductor surrounded by a biocompatible plastic such as polyurethane, PTFE, silicone rubber or the like. Because connector pin 32 has a diameter that is similar to the diameter of lead body 20, the introducer system as illustrated in FIGS. 1 and 2 may be removed from the lead by simply pulling the introducer sheath proximal ends over the lead body.

Figure 4:
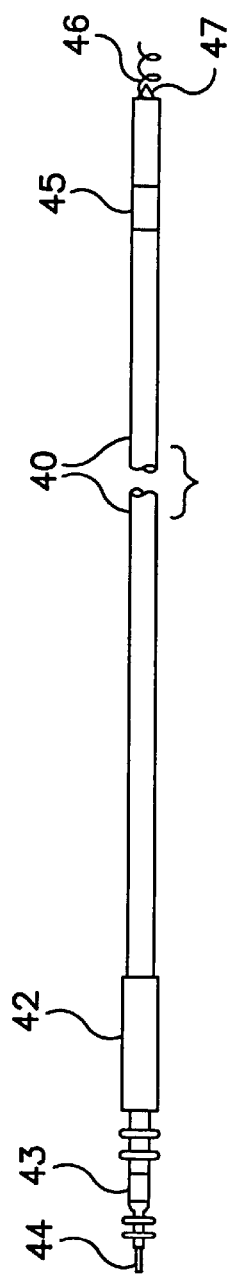
FIG. 4 is a plan drawing of an alternate embodiment of an electrode lead appropriate for introduction through an introducer sheath according to the present invention.

FIG. 4 illustrates an alternative embodiment of a lead appropriate for use in conjunction with an introducer according to the present invention. The lead comprises an elongated insulative lead body 40 that contains two conductors extending the length thereof. The first conductor may be, for example, a stranded wire cable, for example as disclosed in U.S. Pat. No. 6,038,472 issued to Williams, and incorporated herein by reference in its entirety, surrounded by an inner insulator of ethylene tetrafluoroethylene (ETFE), which in turn is surrounded by a coil of MP35N alloy, surrounded by an outer insulative sheath of polytetrafluoroethylene (PTFE). At the distal end of the lead is an electrode 47 which may be fabricated of a porous sintered platinum/iridium alloy, provided with a coating of, or impregnated with, an anti-inflammatory glucocortico steroid such as dexamethesone or beclamethasone as disclosed in U.S. Pat. No. 5,987,746 to Williams incorporated herein by reference in its entirety. A fixation helix 46 serves to allow the electrode 47 to be anchored into adjacent heart tissue. Electrode 47 is coupled, via the inner cable conductor to connector pin 44, located on connector assembly 42 at the proximal end of the lead. A ring electrode or indifferent electrode 45 is shown mounted proximal to electrode 47 and is coupled to a connector ring 43 on connector assembly 42. Fixation helix 46 is rotated by rotation of the lead body in order to imbed the helix in heart tissue, holding electrode 47 to adjacent tissue to be sensed or paced. In alternative embodiments, the helix 46 may be electrically coupled to the electrode 47 and serve as part of the electrode or the helix 46 may be the only electrode, with a release device for delivery of the steroid substituted for electrode 47.

Figure 5:
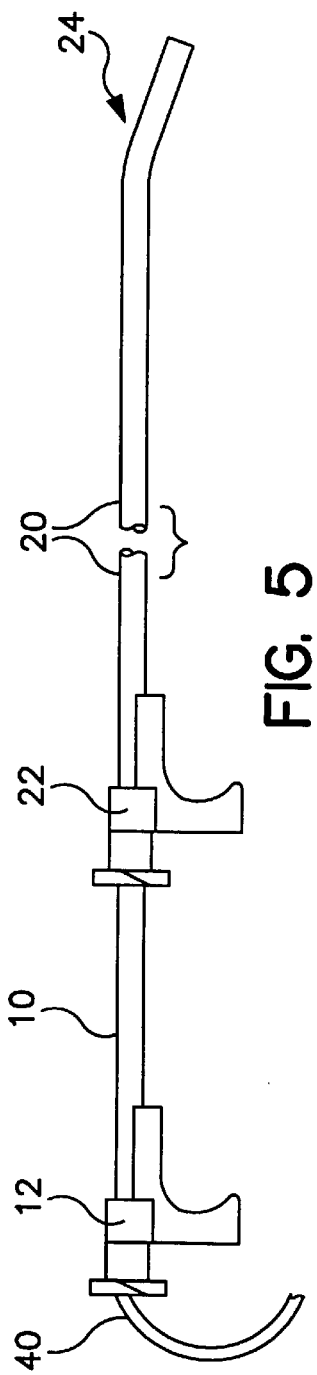
FIG. 5 is a plan view of an introducer according to the present invention with an electrode lead installed, with the distal ends of the lead and the inner sheath retracted into the outer sheath.

FIG. 5 illustrates the introducer components illustrated in FIGS. 1 and 2 and assembled in preparation for implant of a lead as illustrated in FIG. 3 or 4. As illustrated, the body 10 of the inner introducer sheath is inserted through the slittable luer hub 22 of the outer introducer sheath, and the lead 40 is introduced through slittable luer hub 12 into the body 10 of the inner introducer sheath. The inner sheath is generally braided with stainless steal to prevent kinking, and to increase torsional rigidity. As initially positioned, the distal end of the inner introducer sheath body 10 is located within and proximal to the distal end of the outer introducer sheath body 20. In this configuration, the flexural rigidity of the PEEK outer introducer sheath body 20, which is greater than that of the inner sheath, causes the inner sheath body 10 to generally assume the configuration of the outer sheath body 24.

Figure 6:
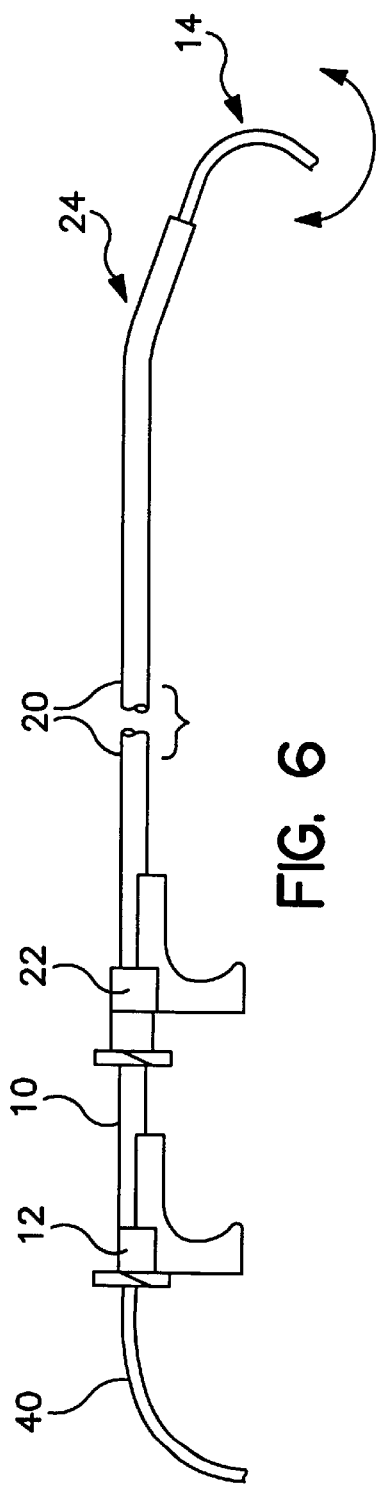
FIG. 6 is a plan view of the introducer and lead of FIG. 5 with the inner sheath advanced out the distal end of the outer sheath, allowing for adjustment of the displayed curvature of the distal portion of the sheath.

FIG. 6 illustrates the apparatus illustrated in FIG. 5, in which the inner introducer sheath body 10 has been moved distally relative to the outer introducer sheath body 20, so that the curve 14 on the distal end of the inner introducer sheath body 10 is now visible. The inner introducer sheath body 10 may also be rotated thru 360° relative to the outer introducer sheath body to provide composite, three-dimensional curvatures. The distal end of the inner introducer sheath body 10 may also be partially withdrawn into the distal end of the outer introducer sheath body 20 in order to provide a displayed curvature of less than 90°. Longitudinal and rotational movement of the inner and outer introducer sheath bodies relative to one another thus allows for the provision of a substantial number of different two and three-dimensional curvatures. The ability to reconfigure the introducer assists in steering it through the patient's vascular system and, in the specific embodiment illustrated, assists in navigating through the vasculature of the patient's heart.

Figure 7:
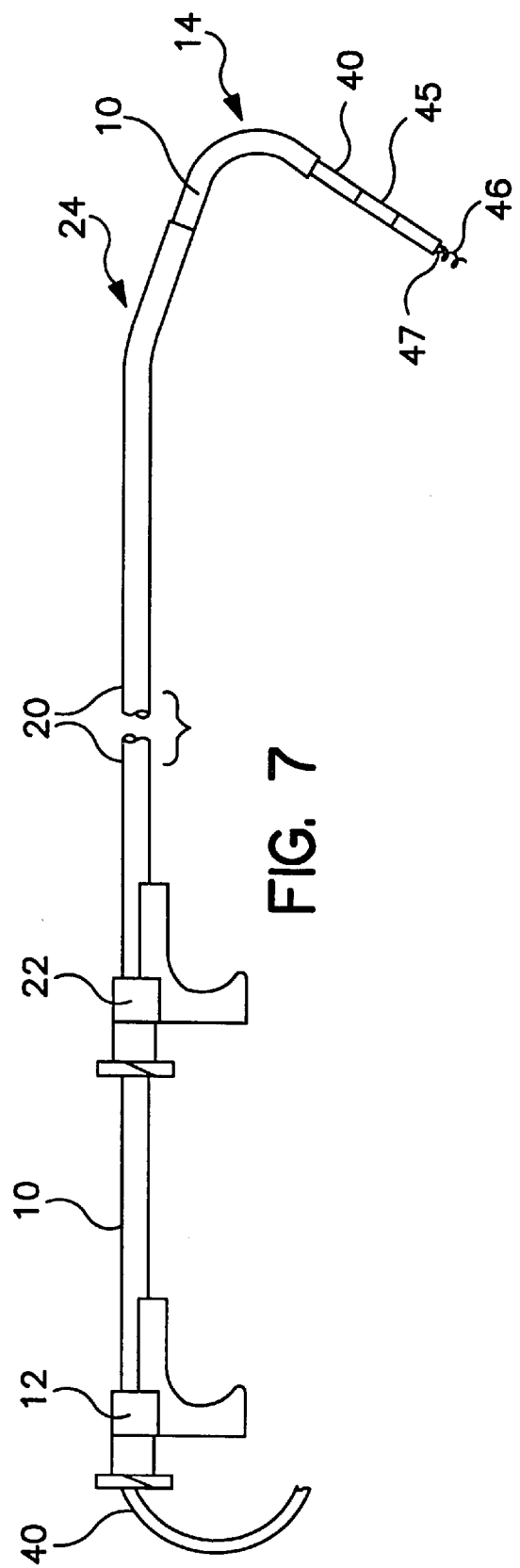
FIG. 7 is a plan view of the introducer and lead of FIG. 5, illustrating advancement of the lead out the distal end of the introducer.

FIG. 7 illustrates the introducer and lead assembly of FIGS. 5 and 6, showing the distal portion of lead body 40 advanced out of the distal portion of inner introducer sheath body 10, facilitating placement of electrode 47 adjacent stimulable tissue and allowing rotation of lead body 40 to imbed fixation helix 46 adjacent the stimulation site. All other numbered elements correspond to those discussed in conjunction with FIGS. 5 and 6 above. In an alternative embodiment, the electrode may be configured as a helix to be imbedded in cardiac tissue such that a separate fixation device is not necessary.

Figure 8:
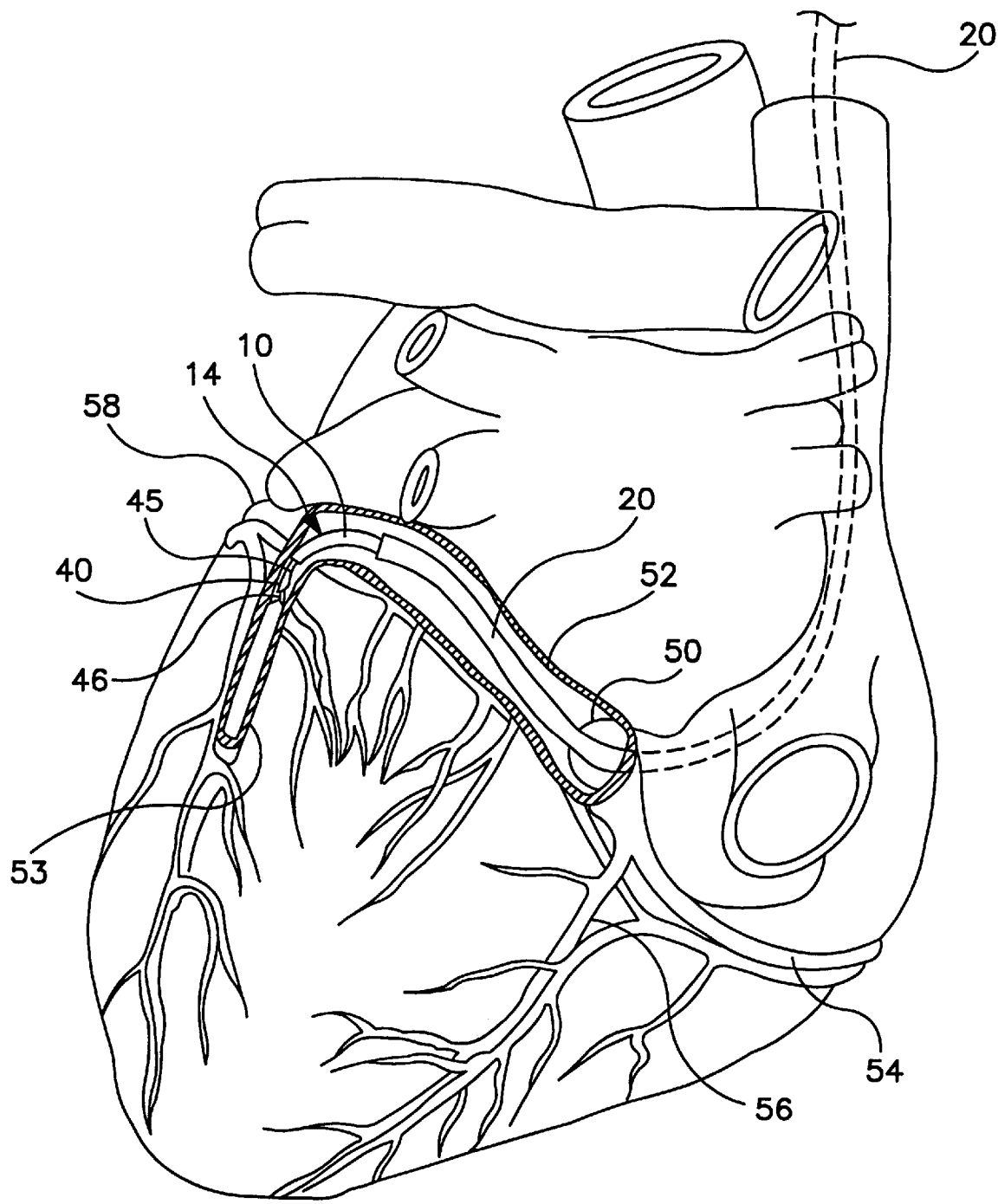
FIG. 8 is an illustration of the introducer of the present invention in conjunction with an electrode lead, illustrating use of the introducer sheath to place a lead in the coronary vasculature of a patient's heart.

FIG. 8 is an illustration of a human heart showing the introducer system of the present invention as employed to place a lead as illustrated in FIG. 4 in the coronary vasculature. In use, the introducer and lead assembled as in FIG. 5 are first passed into the atrium of the heart through the superior vena cava and the distal end of the outer sheath body 20 is advanced into the ostium 50 of the coronary sinus 52. This could be done, for example, to place an electrode to pace the atrium. The introducer may then be pushed distally until the distal end of the outer introducer sheath body 20 is located proximate the desired blood vessel in which the lead is to be located. As illustrated, the lead is intended to be located in the left cardiac vein 53. However, the catheter system might also be employed to advance a lead into the middle cardiac vein 56, the great cardiac vein 58 or the right cardiac vein 54, depending on the particular desired location for the electrode lead.

When the introducer and lead assembler are passed through the vasculature and into the heart, it is important to minimize the chance that cardiac tissue may be unintentionally perforated. To this end, the inner sheath, which generally includes an atraumatic distal tip, may be introduced slightly ahead of the outer sheath. Alternatively, the system may be advanced over a guidewire or other small diagnostic catheter/sheath.

In the particular situation illustrated in FIG. 8, when the distal end of the outer introducer sheath 20 is located proximal to the left cardiac vein 53, the distal end of the inner introducer sheath body 10 is advanced distally outward and steered in order to place its distal end into the vein. Once the introducer has accessed the left cardiac vein 53, the lead body 40 may be advanced distally within the vein, and ultimately positioned at a desired location in the vein by rotation of the lead body 40 to screw fixation helix 46 into cardiac tissue at a desired site for stimulation.

In the embodiments illustrated above, a system is disclosed which is optimized for placement of electrode leads in the coronary vasculature. However, the basic introducer structure described, in conjunction with different defined curvatures formed in the distal portions of one or both of the inner and outer introducer sheath bodies may be used to place leads or catheters at numerous other locations within the body, such as in the coronary sinus. The advantage provided by the combination of an inner sheath body member surrounded by an outer sheath formed of PEEK polymer of minimal wall thickness is believed applicable across a variety of other possible applications, including introduction of leads into other locations within the patient's heart or vascular system, introduction of diagnostic catheters through other portions of the patient's vascular system, and introduction of therapeutic or stimulation catheters for muscle stimulation, nerve stimulation, drug delivery or the like to other locations within the body.

The above embodiments include an outer sheath formed of PEEK polymer. As stated above, PEEK is used because it is remarkably stiff and has a low friction coefficient. An alternative material for use in the outer sheath is a high-performance polyimide manufactured by MicroLumen, Inc. of Tampa Fla. Yet another alternative is rigid polyamides (nylons).

In all embodiments of the current invention, the relative stiffness of the outer sheath as compared to the stiffness of the inner sheath is of critical importance. For example, a relatively flexible neurological catheter, or inner sheath, may not need the flexural rigidity of PEEK to straighten it. A less stiff, but otherwise similar aliphatic polyketone (PEK) may be used. For example, CARILON D26HM100 polymer manufactured by Shell Chemicals may provide the desired straightening properties without resulting in a composite stiffness that is considered too great for neurological interventions.

In conjunction with the above application, we claim:

1. A system comprising:
   a tubular inner introducer sheath having an outer diameter;
   a tubular outer introducer sheath formed of PEEK polymer and having a wall thickness of about 0.005" or less, slidably mounted around the inner introducer sheath; and
   a lead slidably located within the inner introducer sheath.

2. The system of claim 1, wherein the inner introducer sheath is provided with a pre-formed curvature adjacent a distal end thereof.

3. The system of claim 1 or claim 2, wherein the outer introducer sheath is provided with a pre-formed curvature adjacent a distal end thereof.

4. The system of claim 3, wherein the pre-formed curvature of the outer introducer sheath has a radius of between 0.3 and 2 inches.

5. The system of claim 3, wherein the pre-formed curvature of the outer introducer sheath has an arc of approximately 70°.

6. The system of claim 3 wherein the outer introducer sheath fits around the inner introducer sheath with a clearance of about 0.007" or less.

7. The system of claim 2, wherein the pre-formed curvature of the inner introducer sheath has an arc of approximately 90°.

8. The system of claim 2, wherein the pre-formed curvature of the inner introducer sheath has a radius of between 0.3 and 1.0 inches.

9. The system of claim 1 or claim 2 wherein the outer introducer sheath fits around the inner introducer sheath with a clearance of about 0.007" or less.

10. The system of claim 1, wherein the inner introducer sheath includes a slittable luer hub.

11. The system of claim 1, wherein the outer introducer sheath includes a slittable luer hub.

12. The system of claim 1, wherein the lead carries a conductor.

13. The system of claim 12, wherein the conductor of the lead is a coiled conductor.

14. The system of claim 1, wherein the lead has a diameter of between approximately one to two French.

15. The system of claim 12, wherein the conductor is coupled to an electrode.

16. A system comprising:
a tubular inner introducer sheath having an outer diameter; and
a tubular outer introducer sheath formed of a material selected from the group of materials consisting of PEEK and PEK polymers, and having a wall thickness of about 0.005" or less, slidably mounted around the inner introducer sheath.

17. The system of claims 16 wherein the inner introducer sheath is provided with a pre-formed curvature adjacent a distal end thereof.

18. The system of claims 16 or claim 17, wherein the outer introducer sheath is provided with a preformed curvature adjacent a distal end thereof.

19. The system of claim 18, and further including a catheter located within the inner introducer sheath.

20. The system of claim 18, and further including a lead located within the inner introducer sheath.

21. The system of claim 20, wherein the lead carries a conductor.

22. The system of claim 20, wherein the lead has a diameter of between approximately one to two French.

23. The system of claim 20, wherein the conductor of the lead is a coiled conductor.

24. The system of claim 20, wherein the conductor is coupled to an electrode.

25. The system of claim 20, wherein the conductor includes a connector pin adjacent a proximal end thereof.

26. The system of claim 25, wherein the connector pin is isodiametric to the outer introducer sheath.

27. The system of claim 18, wherein the pre-formed curvature of the outer introducer sheath has a radius of between 0.3 and 2 inches.

28. The system of claim 18, wherein the pre-formed curvature of the outer introducer sheath has an arc of approximately 70°.

29. The system of claim 18 wherein the outer introducer sheath fits around the inner introducer sheath with a clearance of about 0.007" or less.

30. The system of claim 16, wherein the inner introducer sheath includes a slittable luer hub.

31. The system of claim 16, wherein the outer introducer sheath includes a slittable luer hub.

32. The system of claim 16 or claim 17 wherein the outer introducer sheath fits around the inner introducer sheath with a clearance of about 0.007" or less.

* * * * *